United States Patent
Juusela

[19]

[11] Patent Number: 6,041,779
[45] Date of Patent: Mar. 28, 2000

[54] POWDER INHALER

[75] Inventor: Petri Juusela, Jyväskylä, Finland

[73] Assignee: Orion Corporation, Espoo, Finland

[21] Appl. No.: 09/068,468

[22] PCT Filed: Nov. 8, 1996

[86] PCT No.: PCT/FI96/00602

§ 371 Date: Aug. 6, 1998

§ 102(e) Date: Aug. 6, 1998

[87] PCT Pub. No.: WO97/17097

PCT Pub. Date: May 15, 1997

[30] Foreign Application Priority Data

Nov. 10, 1995 [FI] Finland ................................. 955441

[51] Int. Cl.$^7$ ................................................ A61M 16/00
[52] U.S. Cl. .................... 128/203.15; 128/203.12; 128/203.19; 128/205.23
[58] Field of Search ............... 128/203.15, 203.12, 128/200.24, 203.19, 205.23; 604/58

[56] References Cited

U.S. PATENT DOCUMENTS

| | | | |
|---|---|---|---|
| 4,274,403 | 6/1981 | Struve | 128/203.15 |
| 5,113,855 | 5/1992 | Newhouse | 128/203.15 |
| 5,857,457 | 1/1999 | Hyppola | 128/203.15 |

FOREIGN PATENT DOCUMENTS

| | | |
|---|---|---|
| 79478 | 5/1983 | European Pat. Off. . |
| 166294 | 1/1986 | European Pat. Off. . |
| 2165159 | 4/1986 | United Kingdom . |
| 86/05991 | 10/1986 | WIPO . |
| 92/00771 | 1/1992 | WIPO . |
| 92/09322 | 6/1992 | WIPO . |
| 95/07724 | 3/1995 | WIPO . |

*Primary Examiner*—John G. Weiss
*Assistant Examiner*—V. Srivastava
*Attorney, Agent, or Firm*—Finnegan, Henderson, Farabow, Garrett & Dunner, LLP

[57] ABSTRACT

The invention relates to a device for the dispensing of a powdered medication by inhalation. The device comprises a medicament container, an air channel, a metering member equipped with a dosing recess, and a counter for the number of doses remaining in the medicament container. The counter comprises a mechanism which detects, upon the returning of the metering member into the filling position, whether or not the dose has been inhaled from the dosing recess.

15 Claims, 4 Drawing Sheets

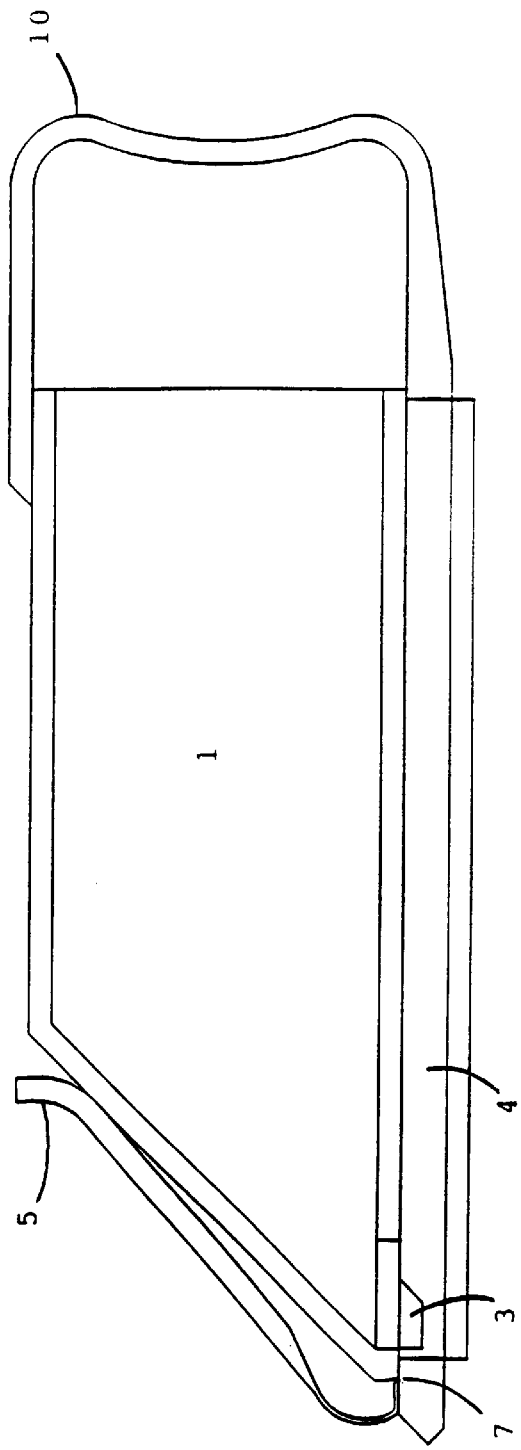
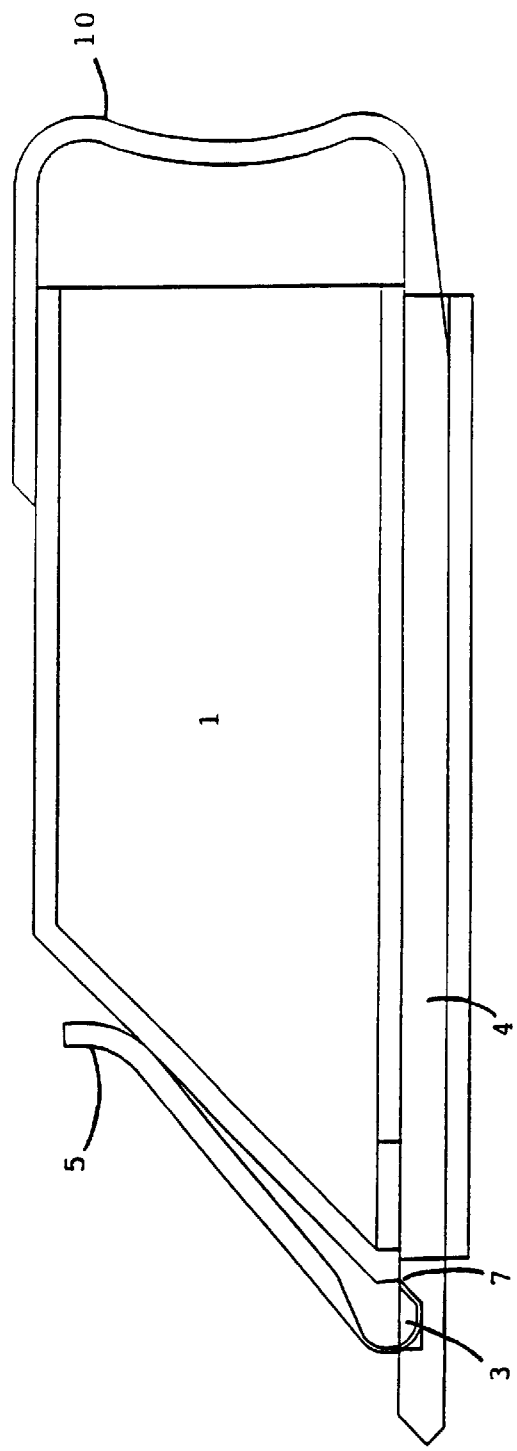
Fig 3a
Fig 3b

POWDER INHALER

BACKGROUND OF THE INVENTION

The invention relates to a device for dispensing of a powdered drug preparation by inhalation. The device is in particular a multiple-dose device without propellant gas, equipped with a metering means which dispenses doses from a powder container. A device such as this is usable, for example, in the treatment of asthma.

The administering of a powdered drug preparation by inhalation from an inhaler is commonly known. Multiple-dose type powder inhalers comprising a flow container which holds the drug and a metering member which measures and dispenses a unit dose are also known, for example from patent publications GB 2165159, EP 79478, and EP 166294. In these devices, a series of dosing recesses are notched into the surface of a cylindrical metering member, and the said member is disposed in a chamber of precisely the same shape. When the metering member is rotated, the dosing recesses in turn will move first to a position in alignment with the powder container for being filled and thereafter to a position in alignment with the inhalation channel, whereupon a unit dose will fall by gravity from the dosing recess into the inhalation channel. Thereafter the dose of medicament is inhaled from the inhalation channel. These devices have the drawback that they make overdosing of the medicament possible by allowing the dispensing of a plurality of doses in succession into the inhalation channel, whereby a multiple dose may be drawn by one inhalation.

Attempts have been made to solve the above-mentioned problem by using dispensing systems in which the dosing recess will not be emptied into the inhalation channel by gravity but, instead, the dose of medicament is inhaled directly from the dosing recess, such recesses having been notched into the surface of a metering member having the shape of a cylinder, a cone or a truncated cone, as disclosed in patent publications WO 92/00771 and WO 92/09322. Also in these devices, a metering member having the shape of a cylinder, a cone or a truncated cone is disposed in a chamber having precisely the same shape. When the metering member is rotated, the dosing recesses will move first to a position in alignment with the flow container for filling, and then to the inhalation channel, which is shaped so that the dosing recess will be emptied under the effect of the air flow being inhaled, and thereafter, having rotated through a full 360°, back to a position in alignment with the flow container. Since the metering member is, for purposes of metering precision, disposed within a chamber of the same shape, and since it has to be rotated through 360°, most of which is futile for the actual function of the inhaler, in such devices the metering member may be prone to jamming as powder falls onto the surfaces of the device.

In patent publications WO 92/00771 and WO 92/09322 referred to above there is additionally disclosed a counter system the purpose of which is to indicate the quantity of unit doses which remain in the inhaler or which have already been used. The operating mechanism of these counters is linked to the rotary movement of the metering member, which movement is transmitted to a geared counting disk or coiled strip. The disc or strip is equipped with markings which can be seen on the outside of the inhaler. The said counters thus in fact indicate how many times the metering member has been moved to the inhalation channel or how many times the inhaler has been activated for inhalation. However, the patient may for various reasons activate such an inhaler also without the purpose of inhaling, in which case the unit dose is ultimately returned to the powder container. Thus the said counters do not always indicate the real number of remaining unit doses.

BRIEF SUMMARY OF INVENTION

The present invention relates to a powder inhaler which comprises a medicament container containing a plurality of medicament doses; an air channel through which air is drawn via a mouthpiece; a metering member equipped with a dosing recess, the metering member being movable from a first position, in which the dosing recess is filled with powder coming from the medicament container, to a second position, in which the dosing recess is in the air channel; and means for indicating the number of doses remaining in the medicament container, said indicator means comprising a mechanism to detect whether or not the dosing recess is substantially free of medicament upon the return of the metering member from the second position to the first position.

If the dosing recess is substantially free of medicament when the metering member returns from the second position to the first position, the counter according to the invention will register that one unit dose has been consumed from the medicament container. If, on the other hand, the dosing recess is still full of medicament when the metering member returns from the second position to the first position, the counter will not register the dosing. The counter thus detects whether or not the powder dose has been inhaled from the dosing recess. Thus the counter indicates the actual number of doses remaining in the medicament container.

The mechanism comprised by the indicator means of the inhaler according to the invention preferably comprise a counting member communicating with the dosing recess. The counting member is preferably constructed so that there is between the first position and the second position of the metering member a third position, in which the counting member tends to fall into the dosing recess if the recess is substantially free of medicament.

The indicator means also comprise a display the markings of which can be distinguished on the outside of the inhaler. Such a display is preferably a counting disc equipped with dose quantity markings.

In one preferred embodiment of the invention the counting member is attached to the counting disc. As the counting member falls into the dosing recess, the counting disc attached to it moves downwards. In this case the inhaler is equipped with a spike-like projection, against which the downwards moving counting disc impinges, causing the counting disc to rotate. Step-by-step rotation of the counting disc can be effected, for example, by providing the counting disc with gears which the spike-like projection is arranged to engage. The spike-like projection is preferably located on the surface of the metering member. The arrangement of the gears of the counting disc so as to rotate the counting disc stepwise can be implemented in ways known to one skilled in the art.

The counting member is arranged in the inhaler preferably so that it rests against the surface of the metering member and is disposed outside the medicament container. As the metering member moves between the filling position and the inhalation position, the counting member is in sliding contact with the surface of the metering member so that it will be in alignment with the dosing recess when the metering member is in a predetermined position between its two extreme positions. If the dosing recess is substantially free of medicament as the recess arrives from the inhalation position to the filling position, the counting member will fall into the recess when the recess is in alignment with the counting member, and will rise again to the surface of the metering member when the empty recess moves from a position in alignment with the counting member towards the filling position in the medicament container. If the recess is full of medicament, the counting member will not substantially fall into the dosing recess so as to cause the counting disc to rotate but will slide over it.

When the counting member is resting against the surface of the metering member it should load the metering member with a force which is of a sufficient magnitude to cause the counting member to fall into the recess when the recess is substantially free of medicament. On the other hand, the loading force should be so small that, when the recess is full of medicament, the counting member substantially slides over the recess without falling into the recess. A suitable loading can be effected in various ways, for example, by using springs. Preferably the loading is effected by attaching the counting member flexibly by means of a plastic membrane hinge to, for example, the medicament container. A membrane hinge is produced by thinning the plastic material so that in the area of the thinning (membrane) there is formed a flexible hinge. If the inhaler is made of the same plastic, the counting member may be integral with the medication container, in which case the counting member is linked to the container by means of a membrane hinge. The load can be adjusted by changing the thickness of the membrane.

Instead of a mechanically operating counting member as described above, the detector mechanism may also be based on an other principle, giving a positive signal when the dosing recess is substantially free of medicament powder. The signal may be, for example, electronic. In that case the mechanism preferably comprises an electronically operating counting member communicating with the dosing recess, e.g. a pressure transducer or a photoelectric cell, which is connected to an electronically operating display, such as a liquid crystal display. If the counting member is a photoelectric cell, the metering member is made of transparent material. The application of an electronically operating counting member in the device according to the invention can be effected in ways which are known to one skilled in the art.

The metering member of the inhaler preferably comprises a slide which is movable in its longitudinal direction from a first position, in which the dosing recess is filled with powder coming from the medicament container, to a second position, in which the dosing recess is in the air channel, the medicament powder being maintained in the dosing recess by the support of the recess bottom, and the air channel being positioned so that, during the inhalation the air flow releases the powder directly from the dosing recess. Such a structure prevents the simultaneous inhaling of a plurality of doses. Furthermore, the risk of the metering member jamming is small, since the movement of the surfaces rubbing against each other is slight.

Also other metering member alternatives, for example cylindrical or conical metering members, are usable in the device according to the invention.

LIST OF DRAWINGS

The principle of the device according to the invention is illustrated below by way of example, with reference to FIGS. 1–4c.

FIG. 3a is a cross-sectional representation of the container, metering member and counting member of the device according to the invention, with the metering member in the filling position.

FIG. 3b is a cross-sectional representation of the container, metering member and counting member of the device according to the invention, with the dose recess of the metering member in alignment with the counting member.

DETAILED DESCRIPTION

Figure 1:
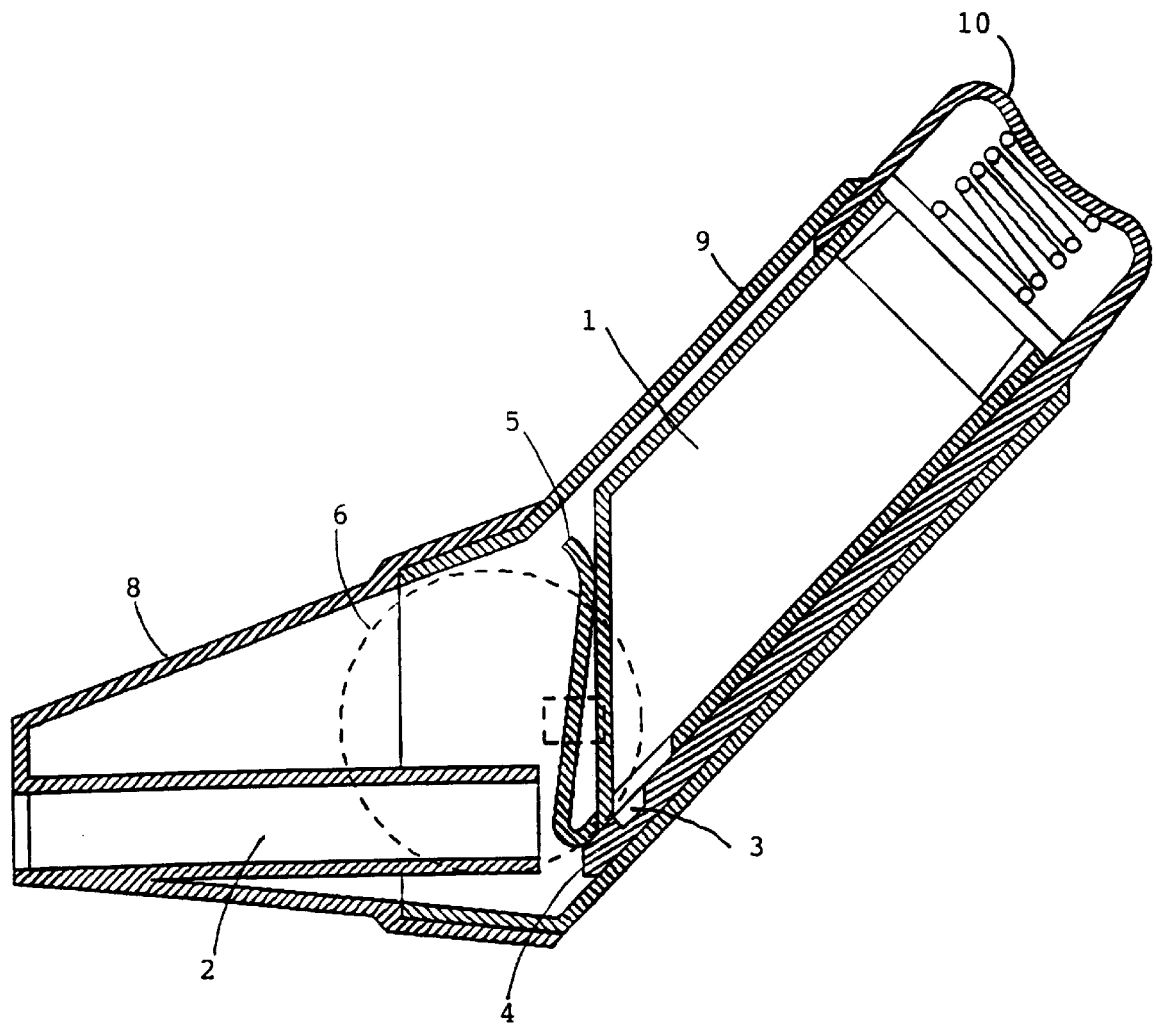
FIG. 1 is a cross-sectional representation of a powder inhaler according to the invention.
Figure 2:
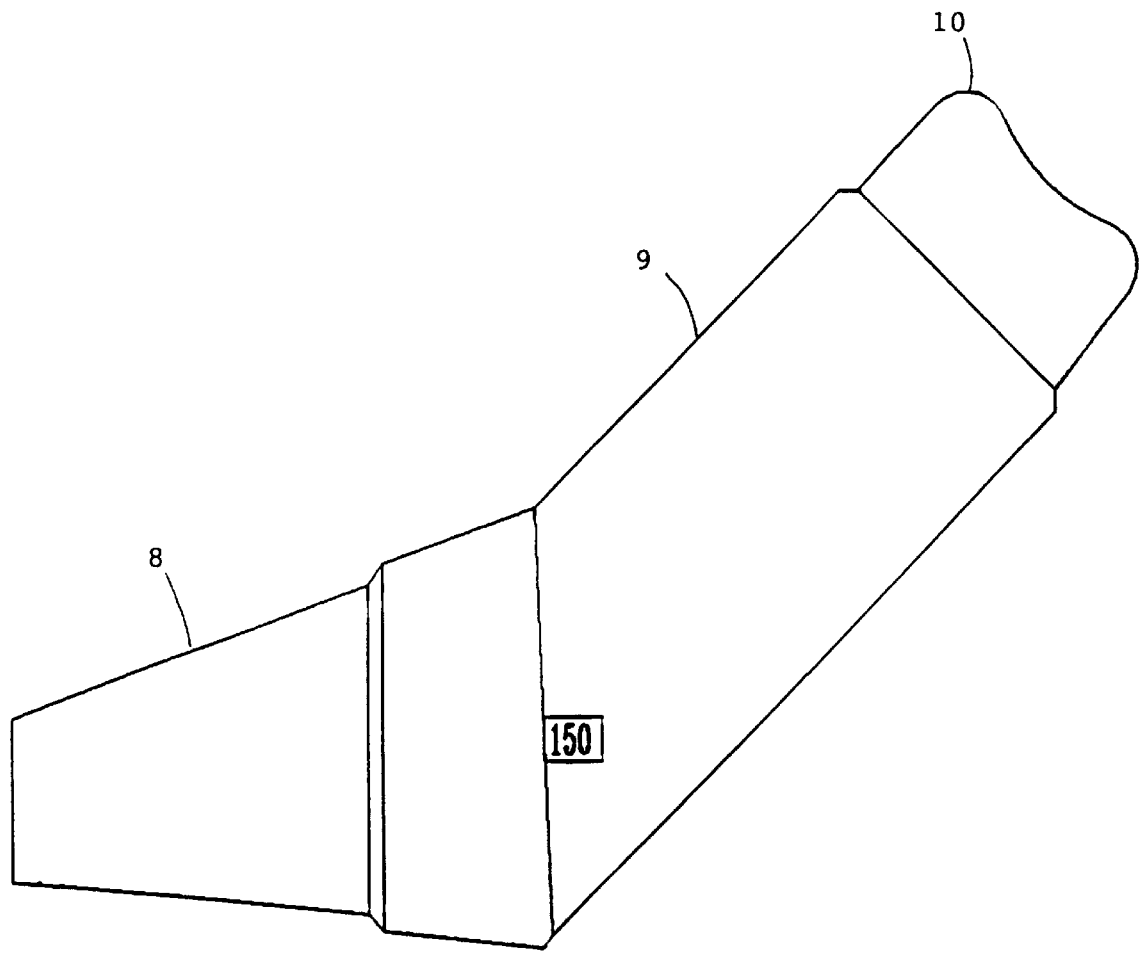
FIG. 2 shows a side view of the exterior of the device of FIG. 1.

Referring to FIGS. 1 and 2, the device according to the invention comprises a mouthpiece (8) and an outer casing (9), the principal axes of which are at an angle of 45° to each other. The cross-section of the outer casing and of the mouthpiece is rectangular. The outer casing has a window for the display of the counting disc. Inside the outer casing there is a medicament container (1) closed with a cap, the cross-section of the container also being rectangular. The lower section of the container is slanted to facilitate the flow of the powder from the container towards the flow aperture. Below the flow aperture of the container there is a strip-like metering member (4) equipped with a dosing recess (3), the metering member being movable in its longitudinal direction between two extreme positions, i.e. the filling position and the inhalation position.

In the filling position, which is the normal resting position of the metering member, the dosing recess (3) of the metering member (4) is under the flow aperture of the container, at which time the dosing recess becomes filled with powder coming from the container. The metering member can be transferred by means of a plunger (10) to the inhalation position, whereby the dosing recess is moved from the container into the air channel (2). The medication is inhaled through the mouthpiece (8) while the plunger (10) is depressed, at which time the metering member is in the inhalation position. The mouthpiece (8) constitutes part of the air channel (2) through which the air to be inhaled is drawn. The air inlets and possible air flow guides, which are not indicated in the figures, are arranged so that the air flowing in will impinge against the dosing recess and will release the medicament powder directly from the dosing recess into the air to be inhaled. The plunger (10) is equipped with a return mechanism, in this case a spring, which will return the metering member to the filling position when the plunger is released.

The operation of the counting mechanism is best seen in FIGS. 3 and 4. FIG. 3a shows a cross-section of the container (1), the metering member (4) and the counting member (5), with the metering member in the filling position. FIG. 3b is the same as 3a, except that the dosing recess (3) of the metering member is in alignment with the counting member (5) and substantially free of medicament. FIG. 3a shows the counting member (5), which is attached to the container at point (7) by mediation of a flexible membrane hinge The membrane hinge is made up of a plastic material, for example polypropylene, in which there has been made a hinge-like flexible thinning (membrane). The container, the membrane hinge and the counting member are in this case of the same piece, made from plastic. The thinned area of the counting member rests folded against the metering member and loads it with a weak force due to the fold. The force is adjusted so that when the metering member is transferred to the inhalation position by a depression of the plunger (10), the counting member will slide over a full dosing recess without falling into the recess. FIG. 3b depicts a situation in which the dose has been inhaled from the dosing recess while the metering member has been in the inhalation position, and the plunger (10) has been released. The empty dosing recess has arrived at the counting member, whereupon the force due to the folding of the membrane hinge is sufficient to cause the counting member to fall into the recess. As the metering member continues to move towards the filling position, the counting member will again rise to its normal position.

Figure 4B:
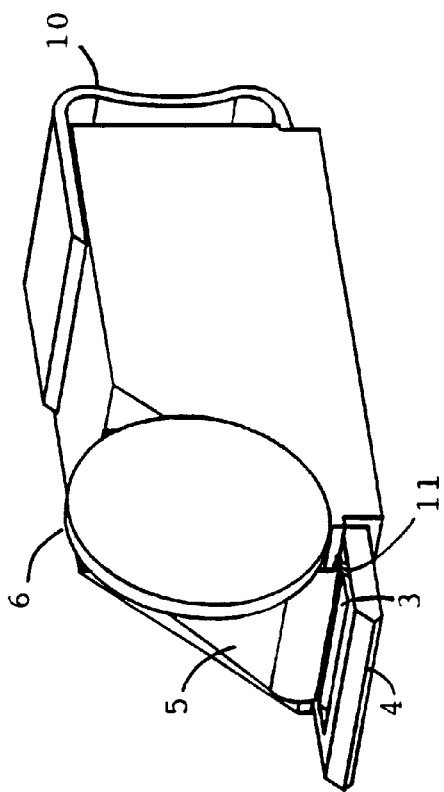
FIG. 4b is a perspective representation of the container, metering member and counting mechanism of the device of FIG. 3a or b, with the metering member in the inhalation position.
Figure 4A:
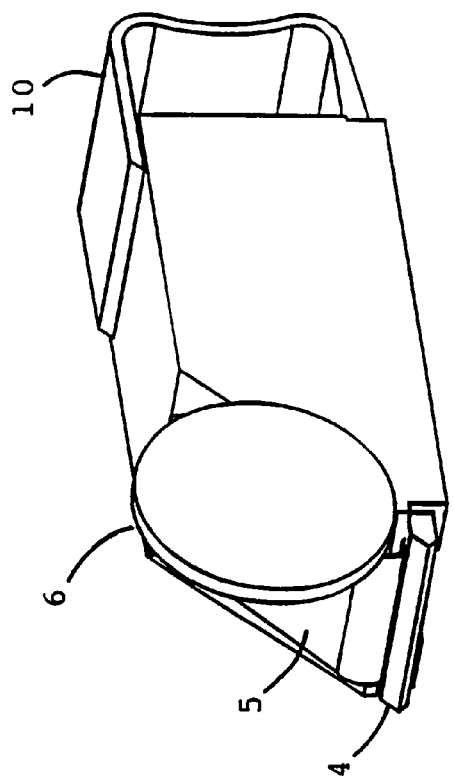
FIG. 4a is a perspective representation of the container, metering member and counting mechanism of the device of FIG. 3a or b, with the metering member in the filling position.
Figure 4C:
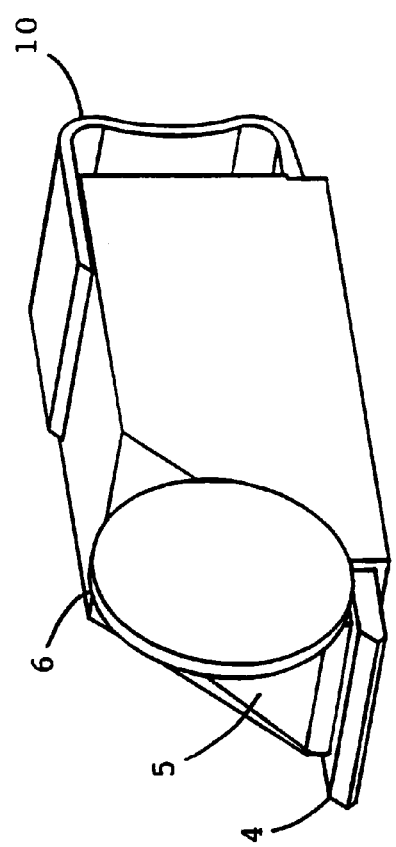
FIG. 4c is a perspective representation of the container, metering member and counting mechanism of the device of FIG. 3a or b, with the metering member in alignment with the counting member.

FIGS. 4a, b and c show the counting disc (6) to which the counting member is attached. The exterior surface of the counting disc is equipped with markings indicating the number of doses and the interior surface with gears (not visible in the Figure). In FIG. 4a the metering member is in the filling position, and the counting member and the counting disc are in their upper position. In FIG. 4b the plunger (10) has been depressed, whereupon the metering member has moved to the inhala-tion position. On the surface of the metering member there is seen a spike-like projection (11) for rotating the counting disc. For the movement of the projection (11) the container wall has an aperture (not seen in the Figure). In FIG. 4c the plunger has been released and the counting member has fallen into the dosing recess. At the same time the counting disc attached to the counting member has fallen downwards so that the spike-like projection engages the gears provided on the interior surface of the counting disc, causing the counting disc to rotate.

I claim:

1. A device for dispensing a powdered medicament by inhalation, comprising a medicament container (1) which contains a plurality of medicament doses; an air channel (2) through which air is drawn via a mouthpiece; a metering member (4) equipped with a dosing recess (3), the metering member being movable from a first position, in which the dosing recess is filled with powder coming from the medicament container, to a second position, in which the dosing recess is in the air channel; and means for indicating the number of doses remaining in the medicament container, characterized in that said indicator means comprise a mechanism to detect whether or not the dosing recess (3) is substantially free of medicament powder upon the return of the metering member (4) from the second position to the first position.

2. A device according to claim 1, characterized in that said mechanism comprises a counting member communicating with the dosing recess.

3. A device according to claim 2, characterized in that the counting member is a electronically operating counting member.

4. A device according to claim 3, characterized in that the electronically operating counting member is a pressure transducer or a photoelectric cell.

5. A device according to claim 2, characterized in that the counting member is a mechanically operating counting member (5).

6. A device according to claim 5, characterized in that there is between the first and second positions of the metering member a third position, in which the counting member (5) tends to fall into the dosing recess if the recess is substantially free of medicament powder.

7. A device according to claim 5, wherein the indicator means comprises a counting disc (6) equipped with markings of the number of doses.

8. A device according to claim 7, characterized in that the counting member (5) is attached to the counting disc (6).

9. A device according to claim 8, characterized in that, when the counting member (5) falls into the dosing recess, the counting disc attached to the counting member (5) will move downwards and will engage a spike-like projection (11), which will cause the counting disc to rotate.

10. A device according to claim 6, wherein the indicator means comprises a counting disc (6) equipped with markings of the number of doses.

11. A device according to claim 10, wherein the counting member (5) is attached to the counting disc (6).

12. A device according to any one of claims 6–9, 10 or 11, wherein the counting member (5) rests against the surface of the metering member (4) and loads it with a weak force.

13. A device according to claim 12, characterized in that the counting member (5) is attached to the container (1) flexibly by means of a membrane hinge.

14. A device according to claim 1 or 6, wherein the metering member (4) comprises a slide which is movable in its longitudinal direction from a first position, in which the dosing recess is filled with powder coming from the medicament container, to a second position, in which the dosing recess is in the air channel, the medicament powder being maintained in the dosing recess by the support of the recess bottom, and the air channel being positioned so that, during the inhalation the air flow releases the powder directly from the dosing recess.

15. A device according to claim 12, wherein the metering member (4) comprises a slide which is movable in its longitudinal direction from a first position, in which the dosing recess is filled with powder coming from the medicament container, to a second position, in which the dosing recess is in the air channel, the medicament powder being maintained in the dosing recess by the support of the recess bottom, and the air channel being positioned so that, during the inhalation the air flow releases the powder directly from the dosing recess.

* * * * *